(12) United States Patent
Ma et al.

(10) Patent No.: US 12,085,535 B2
(45) Date of Patent: Sep. 10, 2024

(54) SYSTEM AND METHOD FOR MEASURING A MULTIPHASE FLUID

(71) Applicant: ENERCORP ENGINEERED SOLUTIONS, LLC, New Castle, DE (US)

(72) Inventors: Lu Ma, Basingstoke (GB); Yessica Arellano, Basingstoke (GB)

(73) Assignee: ENERCORP ENGINEERED SOLUTIONS, LLC, New Castle, DE (US)

( * ) Notice: Subject to any disclaimer, the term of this patent is extended or adjusted under 35 U.S.C. 154(b) by 160 days.

(21) Appl. No.: 17/783,832

(22) PCT Filed: Dec. 18, 2020

(86) PCT No.: PCT/EP2020/087138
§ 371 (c)(1),
(2) Date: Jun. 9, 2022

(87) PCT Pub. No.: WO2021/130129
PCT Pub. Date: Jul. 1, 2021

(65) Prior Publication Data
US 2023/0024801 A1    Jan. 26, 2023

(30) Foreign Application Priority Data
Dec. 23, 2019 (GB) ..................... 1919168

(51) Int. Cl.
*G01N 27/74* (2006.01)
(52) U.S. Cl.
CPC .................. *G01N 27/74* (2013.01)
(58) Field of Classification Search
CPC .. G01F 1/588; G01F 1/60; G01F 1/74; G01N 27/025; G01N 27/74; G01N 33/2823; G01V 3/28
See application file for complete search history.

(56) References Cited

U.S. PATENT DOCUMENTS

| | | | | |
|---|---|---|---|---|
| 5,103,181 A | * | 4/1992 | Gaisford | G01N 33/2823 324/645 |
| 5,341,100 A | * | 8/1994 | Taylor | G01V 3/30 73/152.24 |

(Continued)

FOREIGN PATENT DOCUMENTS

| | | |
|---|---|---|
| GB | 2514114 A | 11/2014 |
| GB | 2575104 A | 1/2020 |
| WO | 2015128704 A1 | 9/2015 |

OTHER PUBLICATIONS

International Preliminary Report on Patentability in related international application No. PCT/EP2020/087138 issued on Jun. 28, 2022.

(Continued)

*Primary Examiner* — Vinh P Nguyen
(74) *Attorney, Agent, or Firm* — MH2 TECHNOLOGY LAW GROUP, LLP (57) ABSTRACT

Apparatus and method are provided wherein by measuring both the electrical permittivity and the electrical conductivity of the measured multiphase fluid, the resultant amplitude and phase angle of the induced complex voltage can be analysed. The phase angle data can be analysed to provide information on the electrically conductive phase, and that information can be employed to analyse the amplitude data, in particular to use the information on the electrically conductive phase to determine the contribution to the amplitude data by the electrically non-conductive phase. This analytical technique enables the electrical permittivity of the electrically non-conductive phase to be accurately determined. By determining the degree of contribution to the complex voltage measurement by both the permittivity and the conductivity, enhanced measurement accuracy of a multiphase fluid can be achieved.

23 Claims, 4 Drawing Sheets

(56) References Cited

U.S. PATENT DOCUMENTS

| | | | |
|---|---|---|---|
| 5,485,743 | A | 1/1996 | Taherian et al. |
| 7,276,916 | B2 * | 10/2007 | Hammer ............ G01N 33/2823 |
| | | | 324/633 |
| 8,076,950 | B2 * | 12/2011 | Wee ................... G01N 33/1833 |
| | | | 73/61.61 |
| 10,753,778 | B2 * | 8/2020 | McCann ................. G01V 3/10 |
| 11,085,803 | B2 * | 8/2021 | Machuca .................. G01F 1/74 |
| 11,385,084 | B2 * | 7/2022 | Godager ............... G01N 27/06 |
| 11,417,506 | B1 * | 8/2022 | Birmingham ........... H01J 9/042 |
| 2010/0127705 | A1 | 5/2010 | Scharfetter |
| 2011/0267074 | A1 | 11/2011 | Xie et al. |

OTHER PUBLICATIONS

Search Report under Section 17 issued by GB Intellectual Property Office in related GB application 1919168.3 issued on Jun. 16, 2020.
International Search Report and Written Opinion in related international application No. PCT/EP2020/087138 issued on Apr. 13, 2021.
"Electromagnetic Technique for Hydrocarbon and Sand Transport Monitoring: Proof of Concept" By Yessica Arellano, et al., IEEE Access, vol. 8, Jun. 30, 2020.

* cited by examiner

SYSTEM AND METHOD FOR MEASURING A MULTIPHASE FLUID

FIELD OF THE INVENTION

The present invention relates to a method of, and an apparatus for, monitoring a multiphase fluid using magnetic induction tomography. The multiphase fluid comprises fluids, and may comprise a mixture of liquids, or one or more liquids in a mixture with solids and/or gases. The fluid may be static or dynamic, for example a multiphase flow in a fluid conduit. This invention particularly relates to a monitoring apparatus and method which has a number of applications, in particular within the oil and gas exploration and production industry.

BACKGROUND

A number of prior patent specifications in the name of the Applicant are directed to the use of Magnetic Induction Tomography (MIT), either used alone or in conjunction with other techniques, for monitoring a multiphase flow in a pipe, in particular in the oil and gas exploration and production industry.

In particular, GB2513678B discloses an "Oil well system and operating method including monitoring multiphase flow in a pipe", GB2513679B discloses a "Method of defining a multiphase flow comprising three phases", GB2507368B discloses "Method and apparatus for monitoring the flow of mixtures of fluids in a pipe", GB2534337B discloses "Method and apparatus for monitoring of the multiphase flow in a pipe" and GB2530601B discloses "Method and apparatus for monitoring of the multiphase flow in a pipe". In addition, GB2527324B discloses a "Segmented Electromagnetic Sensor".

In these prior specifications, transmitting and receiving coils are located around the outside of a pipe. The transmitting coil(s) are supplied with a varying current which transmits electromagnetic field into a multiphase flow within the pipe. The electromagnetic field induces eddy currents in an electrically conductive phase within the pipe resulting in a secondary electromagnetic field. The secondary electromagnetic field induces an electric field which can be measured in the receiving coil(s) via voltage output that can be analysed to determine properties of the multiphase flow.

It is disclosed is these specifications that electromagnetic energy can provide information related to certain physical properties of materials in the multiphase flow exposed to this type of energy. When used in an electromagnetic flowmeter, electrical capacitance tomography (ECT), electrical resistance tomography (ERT) and magnetic inductance tomography (MIT) can be used to interrogate the multiphase flow. In each case a varying electric or magnetic field can be applied across the multiphase flow, and measurements of voltage, current and magnetic field can be used to measure certain physical parameters of the constituent components of the multiphase flow.

It is known to use magnetic inductance tomography (MIT) to measure a contrast in electrical conductivity between, on the one hand, an electrically conductive medium (e.g. an aqueous phase) and, on the other hand, an electrically non-conductive medium (e.g. an oil phase). When measuring fluid conductivity, for example in a multiphase flow, a high frequency (1-30 MHz) magnetic field is typically used. In these conditions, it has been assumed in the state of the art that the displacement current induced by electrical permittivity is small compared to the eddy current induced by electrical conductivity, and therefore the displacement eddy current is ignored. Therefore the electrical permittivity, relating to the dielectric properties of an electrically non-conductive phase, has not been measured using such applications of magnetic inductance tomography (MIT).

It is known in the art to use two separate systems to measure the phase and amplitude of a complex voltage induced by various fluids in a multiphase flow, the two separate systems usually respectively operating at two different frequencies.

It is known to combine an MIT apparatus configured to measure electrical conductivity with another apparatus configured to measure electrical permittivity in a composite system to measure both the electrical conductivity and the electrical permittivity in a region of interest. However, the primary problem with this measurement technique is that the use of two apparatus requires the operation of the respective apparatus, i.e. the MIT apparatus configured to measure electrical conductivity and the other apparatus configured to measure electrical permittivity, to take place in sequence, both in time and in space. This measurement technique therefore suffers from the problem of both temporal and spatial lags between two sets of measurements, i.e. electrical conductivity and electrical permittivity.

A recent paper (Yazdanian, H. and Jafari, R. (2018) 'Improvement on Conductivity Image Reconstruction in Magnetic Induction Tomography', in IEEE Transactions on Instrumentation and Measurement, pp. 1-5) disclosed that magnetic induction tomography (MIT) was used to image the conductivity and permeability properties of a target inside an object based on electrical impedance measurements from excitation and detection coils. Both real and imaginary parts of the induced voltages were used in conductivity image reconstruction for both low and high conductivity applications. The imaginary and real components of the complex voltage were de-multiplexed and the effect on the conductivity and permeability properties were evaluated separately for the imaginary and real components.

Although the prior art summarised above discloses a method of, and a monitoring apparatus for, monitoring a multiphase fluid, for example a flow in a pipe, using magnetic induction tomography (MIT) which can effectively monitor such a multiphase fluid, there is nevertheless a need in the art for an improved monitoring apparatus and method.

In particular, there is a need in the art for a monitoring apparatus and method which has an enhanced sensitivity to distinguish between an electrically conductive phase such as an aqueous phase, for example water, and an electrically non-conductive phase, such as an oil phase or a solid phase such as sand, in a multiphase fluid, for example in a multiphase flow.

SUMMARY OF THE INVENTION

The present invention aims, at least partially, to meet this need in the art, particularly in the field of oil and gas exploration and production, to provide enhanced analytical data in real-time on the phase composition of a multiphase fluid, particularly a multiphase flow within a pipeline used in the oil and gas industry. However the invention also has application for the monitoring of static multiphase fluids, and in other applications in different technical and commercial fields.

The present invention accordingly provides a monitoring apparatus for monitoring a multiphase fluid.

The present invention further provides a method of monitoring a multiphase fluid.

When monitoring a multiphase flow in a pipe using magnetic induction tomography, when the multiphase flow includes an electrically conductive phase, such as an aqueous phase, for example water, various parameters may be relevant to define the performance and accuracy of the monitoring.

The present invention is at least partly predicated on the finding by the present inventors that in a multiphase flow, the permittivity and conductivity of the mixed fluid vary in both the temporal and spatial domains, and both the electrical permittivity-induced displacement current and the electrical permittivity-induced eddy current contribute to the induced magnetic field that results in the measured voltage change.

Unexpectedly, for example as compared to the Yazdanian and Jafari, 2018 paper discussed above, the present inventors have identified that the effect of permittivity in the overall amplitude signal is at least 1 order of magnitude greater than that observed by independently measuring the real and imaginary components separately. This effect is thought to be associated to the inverse effect that the conductivity has on both amplitude components, decreasing the dynamic range of the absolute amplitude signal, and hence increasing the relative impact of the permittivity in the measurement.

Accordingly, the effect of either of these two displacement currents should not be ignored in order to accurately achieve accurate data processing of the multiphase flow using magnetic induction tomography (MIT) apparatus. The temporal, spatial and frequency related permittivity and conductivity changes are all reflected in the changes in the induced electrical voltage which is measured by the magnetic induction tomography (MIT) apparatus.

The induced electrical voltage is a complex voltage having both an amplitude and a phase. The electrical permittivity of the measured multiphase fluid, in particular the electrical permittivity of the electrically non-conductive phase, affects the measured amplitude of the complex voltage and the electrical conductivity of electrically conductive phase affects both the measured amplitude of the complex voltage and the measured phase angle of the complex voltage.

In this specification, the phase angle measurement, typically expressed as $\varphi$ in radians, is defined by the phase angle of the induced complex voltage from a receiving coil relative to a reference due to the induced eddy currents ($J_{eddy}$) around a conductive medium in the region of interest. The phase angle is measured relative to a reference, which is typically relative to the phase of the exciting magnetic field.

In this specification, the phase difference or phase shift, typically expressed as $\lambda\varphi$ in radians, is defined by the difference between the phase angle of the induced voltage from a coil due to a change in conductivity arising from change in medium structure, motion, an external environment (in either the spatial or time domains), as well as frequency-dependent characteristics, relative to a reference, typically the phase angle of the exciting magnetic field.

The present inventors have found that by measuring both the electrical permittivity and the electrical conductivity of the measured multiphase fluid, the resultant amplitude and phase angle of the induced complex voltage can be analysed. The phase angle data can be analysed to provide information on the electrically conductive phase, and that information can be employed to analyse the amplitude data, in particular to use the information on the electrically conductive phase to determine the contribution to the amplitude data by the electrically non-conductive phase. This analytical technique enables the electrical permittivity of the electrically non-conductive phase to be accurately determined. By determining the degree of contribution to the complex voltage measurement by both the permittivity and the conductivity, enhanced measurement accuracy of a multiphase fluid can be achieved.

In other words, the measurement of the properties of the electrically non-conductive phase can be enhanced by calculation from data including the measured properties of the electrically conductive phase.

Also, the data processing can be enhanced to provide a precise fluid phase or flow pattern using MIT.

Furthermore, the permittivity and the conductivity measurements on the multiphase fluid can be carried out using a single combination of a magnetic field generator and a voltage detector, i.e. using a single magnetic induction tomography (MIT) apparatus, thereby avoiding any temporal or spatial variation in the permittivity and the conductivity measurements, which further enhances measurement accuracy and data processing.

Accordingly, the preferred embodiments of the present invention can avoid the need, as known in the state of the art, to use two separate apparatus to measure the phase and amplitude of a complex voltage induced by various fluids in a multiphase flow. The preferred embodiments of the present invention can provide that both the amplitude and phase angle of a complex voltage can be measured, typically simultaneously, using a single magnetic induction tomography apparatus having a common magnetic field generator and voltage detector assembly.

This preferred embodiments of the present invention can provide one magnetic induction tomography apparatus which can be used to measure both the phase shift and amplitude of the complex voltages to continuously monitor and measure the phase fraction, typically the volume phase fraction, of conductive and non-conductive phases in a multiphase flow. The use of only one magnetic induction tomography apparatus to measure both of these parameters, typically simultaneously, can remove the need to co-locate two separate systems, and therefore improves the measurement accuracy as compared to the known use of two separate apparatus.

In particular, the preferred embodiments of the present invention can provide the technical effects and advantages of: simultaneous measurement of the conductivity and permittivity of a multiphase fluid using one MIT apparatus; real time derivation and verification of the conductive and non-conductive phase volumetric fractions from conductivity and permittivity measurements using one MIT apparatus; removing the need to co-locate two separate MIT systems over the same fluid volume, for example over the same pipe cross-section, hence enhancing flow measurement accuracy; and the improved analysed data of the amplitude and phase angle parameters can enable enhanced in-situ flow pattern imaging to be achieved, typically in real time.

The present invention relates specifically to an improved apparatus and method for the use of MIT (Magnetic Induction Tomography) to monitor multiphase fluids, in particular in the application of MIT to measuring multiphase flows in the oil and gas and other industries. The principle of MIT is that electric coils are excited with alternating current that results in the coils producing varying electromagnetic fields. The object of interest is placed within these fields and the varying field induces varying currents within the object that is dependent on the conductivity of the object. The varying currents in the object produce secondary electromagnetic fields that can be received by the same or other coils. The received secondary electromagnetic field in conjunction with the primary imposed electromagnetic field can be used to compute the conductivity contrast between the object and the material that surrounds it. In accordance with the present invention, the computation also generates data representing at least one property of at least one electrically conductive phase in the multiphase fluid and at least one property of at least one electrically non-conductive phase in the multiphase fluid.

In particular, the electrical conductivity of an electrically conductive phase can be accurately measured to enable the spatial, and preferably also the temporal, location of the electrically conductive phase to be accurately determined, and in addition, the electrical permittivity of an electrically non-conductive phase can also be accurately calculated, the calculation using measured phase angle data related to electrical conductivity and amplitude data related to electrical conductivity, and electrical permittivity, to enable the spatial, and preferably also the temporal, location of the electrically non-conductive phase to be accurately determined. The resultant data can be used to produce an image of the multiphase fluid in real time.

In the preferred embodiments of this invention, the amplitude of the measured complex voltage is used to monitor the permittivity properties of the electrically non-conductive phase, and provide output data that can more accurately represent the location of the electrically non-conductive phase in space and optionally time. For a flowing multiphase fluid, the flow measurement and flow pattern can be more accurately measured and identified.

The preferred embodiments of this invention relate to an apparatus and method to measure the flow of mixtures of fluids from a well or group of wells during oil and gas exploration, production or transportation operations. However, it should be understood that the apparatus and method of the present invention may be used in other potential applications, as those skilled in the art will appreciate. For example, the apparatus and method of the present invention may be used in fluid or flow measurement devices, medical MIT Systems involving measurement of low conductivity contrasts of multiphase fluids, optionally multiphase fluid flows, and multiphase fluid process monitoring equipment.

BRIEF DESCRIPTION OF THE DRAWINGS

Embodiments of the present invention will now be described, by way of example only, with reference to the accompanying drawings, in which.

DETAILED DESCRIPTION

Figure 1:
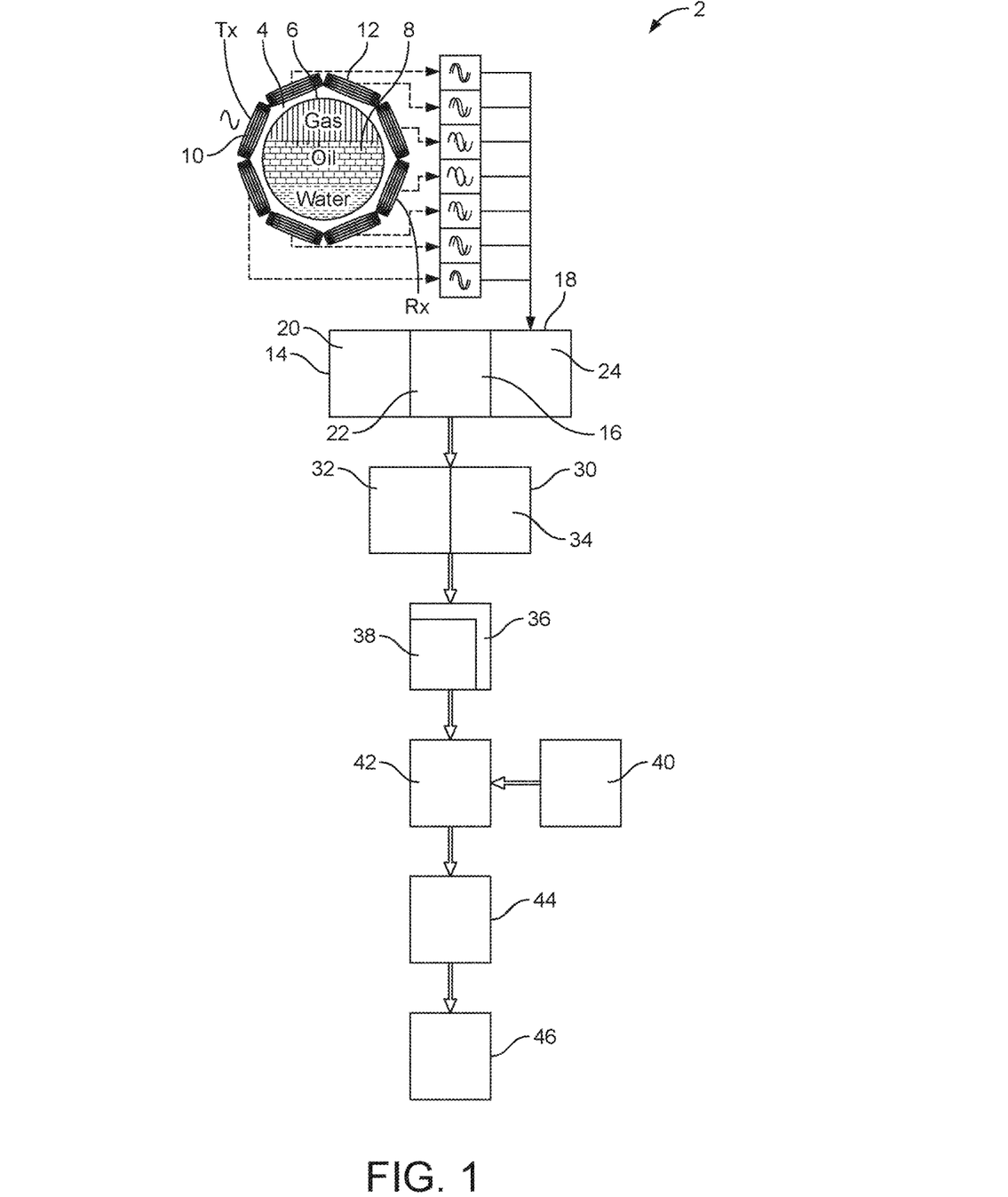
FIG. 1 is a schematic illustration of a monitoring apparatus for monitoring a multiphase fluid, as flow through a pipe, in accordance with an embodiment of the present invention.

Referring to FIG. 1, there is shown a monitoring apparatus 2 for monitoring a multiphase flow in a pipe using magnetic induction tomography. However the apparatus and method of the present invention can be used to monitor any multiphase fluid within an interior volume defined by a body. The multiphase fluid may comprise any mixture of liquid and gas phases, and the liquid phase may comprise aqueous and/or oil phases. Moreover, the multiphase fluid may comprise a solid phase within the fluid. The multiphase fluid may be static or dynamic. The body may be a pipe or any other body for containing a multiphase fluid.

In the illustrated embodiment, the apparatus 2 surrounds a pipe 4 defining a flow conduit 6. In use, a multiphase flow 8 flows along the flow conduit 6 of the pipe 4. The multiphase flow 8 comprises at least two phases, optionally at least three phases, further optionally all of the phases, selected from an oil phase, an aqueous phase, a solid phase and a gaseous phase. In FIG. 1, four phases are shown schematically in stratified form, comprising a continuous gas phase, a continuous oil phase, a continuous aqueous (e.g. water) phase and a continuous solid (e.g. sand). However the apparatus and method of the present invention can be used to monitor both continuous and discontinuous phases in a multiphase fluid. The multiphase flow 8 typically has a primary or continuous phase of the flow, e.g., oil, water or gas, and within the primary phase one or more other phase constituents may be present, for example a solid phase, e.g. sand. The flow regime of these phases can vary significantly depending on the concentrations of each phase and the flow rate. Typically, the phases are not stratified, as shown in FIG. 1, but are irregularly mixed.

A plurality of coils 10, forming a coil assembly 12, are disposed circumferentially around the pipe 4. In the illustrated embodiment, eight coils 10 are disposed circumferentially around the pipe 4, the coils 4 being planar so that the coil assembly 12 forms an octagonal cross-section surrounding the pipe 4. Those skilled in the art will appreciate that more coils could be used to provide more measurements across the pipe 4. Each coil 10 faces an opposite coil 10 of the coil assembly 12, and the opposing coils 10 are on diametrically opposite sides of the pipe 4. Preferably, each coil 10 has a central axis which is orthogonal to a longitudinal axis of the pipe 4, and the central axis of the coils 10 lie in a common plane which is orthogonal to the longitudinal axis of the pipe 4.

The portion of the pipe 4 surrounded by the coil assembly 12 is preferably composed of a material, for example a non-metallic material such as a polymer, which permits electromagnetic field penetration, across a broad wavelength range, emitted from one of the coils 10 to pass through the multiphase material in the flow conduit 6 and then secondary induced electromagnetic radiation to be received by another of the coils 10.

In the illustrated embodiment, each of the coils 10 may be adapted to transmit an electromagnetic field into the flow conduit 6 when energized by an input electrical signal and/or to receive an electromagnetic field from the flow conduit 6 and generate an output electrical signal, as described in detail hereinafter. The coils 10 may alternate between functioning as a transmitter and as a receiver. Accordingly for the illustrated embodiment, in use, each coil 10 is configured to function, in one operating cycle, as a transmitter coil, indicated by Tx, and to function, in a subsequent operating cycle, as a receiver coil, indicated by Rx. However, in an alternative embodiment one or more coils 10 may always function as a transmitter and one or more other coils 10 may always function as a receiver.

In in an alternative embodiment, there can be as few as two coils 10 around the pipe 4. However, preferably there are more than two coils 10 around the pipe 4. Fundamentally, any arrangement or control of the coils 10 may be employed which can transmit an electromagnetic field into multiphase flow 8 in the flow conduit 6 and receive a resultant electromagnetic field from the multiphase flow 8 in the flow conduit 6, and thereby generate an output electrical signal to be used to analyse the phase composition of the multiphase flow 8 using magnetic induction tomography.

In the illustrated embodiment, in a first operating cycle one of the coils 10 is driven as a transmitter and the remaining coils 10 are configured as receivers, so that when there is a total of eight coils 10, seven signals are received by the coils 10 functioning as receivers.

The coils 10 are electrically connected to a controller 18. The controller 18 comprises a driver 20 for providing alternating electrical current, i.e. AC current, at a selected frequency to the transmitter coil(s) 10. Typically, the AC current has a frequency of from 1 kHz to 30 MHz, for example from 1 kHz to 10 MHz. The combination of the coil assembly 12 and the driver 20 comprise a magnetic field generator 14 adapted to generate a magnetic field within the flow conduit 6 of the pipe 4, i.e. within an interior volume defined by a body, the magnetic field temporally varying according to at least one frequency, thereby to apply the varying magnetic field to a multiphase fluid within the volume.

The controller 18 also comprises a voltage measuring system 22, coupled to a processor 24. The voltage measuring system 22 receives the induced electrical current from the receiver coil(s) 10, and can measure an induced complex voltage. Accordingly, the combination of the coil assembly 12 and the voltage measuring system 22 comprise a voltage detector 16 adapted to measure an induced complex voltage which has been produced by electromagnetic induction from at least one phase of the multiphase fluid within the volume.

The voltage measuring system 22 is preferably configured to be sensitive enough to measure voltage amplitudes in a microvolt range (i.e. to an accuracy of +/−1×10$^{-6}$ V) and phase angles to an accuracy of sub-milli degrees (i.e. to an accuracy of +/−1×10$^{-3}$°).

The apparatus 2 further comprises a signal processor 24 for determining, from the measured induced complex voltage, both an amplitude and a phase angle of the complex voltage, thereby respectively to provide amplitude data and phase angle data. The signal processor 24 is adapted to determine the phase angle of the measured induced complex voltage by comparing the phase of the complex voltage and the phase of the magnetic field generated by the magnetic field generator 14. This can provide a measurement of the phase difference between the driving magnetic field and the induced complex voltage, using magnetic induction tomography. The amplitude and a phase angle of the complex voltage are preferably determined simultaneously, and in real time with respect to the magnetic field generator 14 and the voltage measuring system 22.

The apparatus 2 further comprises a data processor 30 for calculating, from the amplitude data and phase angle data, first output data from the amplitude data and second output data from the phase angle data. The first output data is a function of the electrical permittivity, i.e. the dielectric property, and electrical conductivity of the at least one phase of the multiphase fluid. The second output data is a function of the electrical conductivity of the at least one phase of the multiphase fluid. The first and second output data are preferably determined simultaneously, and in real time with respect to the magnetic field generator 14 and the voltage measuring system 22.

The data processor 30 comprises a first module 32 adapted to calculate from the amplitude data a first parameter related to a displacement current induced in at least one electrically non-conductive phase in the multiphase fluid and at least one electrically conductive phase in the multiphase fluid, the first parameter being within the first output data. The data processor 30 also comprises a second module 34 adapted to calculate from the phase angle data a second parameter related to an eddy current induced in at least one electrically conductive phase in the multiphase fluid, the second parameter being within the second output data.

The apparatus 2 further comprises an analyser 36 for processing the first and second output data to generate analysed data representing at least one property of at least one electrically non-conductive phase in the multiphase fluid and at least one property of at least one electrically conductive phase in the multiphase fluid.

The analyser 36 is adapted to generate analysed data which represents, directly or indirectly, the respective phase fractions, preferably volumetric phase fractions, of at least one electrically non-conductive phase in the multiphase fluid and at least one electrically conductive phase in the multiphase fluid. The first and second output data are preferably processed simultaneously, and in real time with respect to the magnetic field generator 14 and the voltage measuring system 22.

In the preferred embodiment, the analyser 36 is adapted to process the first and second output data to generate first analysed data representing the electrical permittivity of the at least one electrically non-conductive phase in the multiphase fluid and second analysed data representing the electrical conductivity of the at least one electrically conductive phase in the multiphase fluid.

The analyser 36 comprises a third module 38 adapted to calculate, from the second parameter related to the at least one electrically conductive phase, a third parameter. The third parameter is related to a contribution to the displacement current of the first parameter by the at least one electrically conductive phase. The third module 38 is adapted to calculate from the first parameter and the third parameter a contribution to the displacement current of the first parameter by the at least one electrically non-conductive phase thereby to generate the first analysed data.

In the preferred embodiment, the apparatus 2 further comprises a memory 40 comprising first stored data representing a relationship between electrical permittivity of at least one known electrically non-conductive phase and amplitude of a complex voltage measured using a magnetic field of known properties. The memory 40 also comprises second stored data representing a relationship between electrical conductivity of at least one known electrically conductive phase and phase angle of a complex voltage measured using a magnetic field of known properties.

The stored data correlating the electrical permittivity and amplitude of a complex voltage, and electrical conductivity and phase angle of a complex voltage has been acquired based upon prior testing of properties of various fluids, and potentially solids suspended in fluids, to be measured using the apparatus and method of this invention, for example, fluids and solids typically extracted from oil fields. The stored data includes parameters from a variety of different geometrical characteristics, multiphase concentrations and operational parameters to provide an electromagnetic model by the stored data. The model may be enhanced by carrying out simulations together with experimental work for each potential multiphase fluid scenario to be tested, in order to increase the sensitivity to the measurement of combined changes in conductivity and permittivity that are relevant to the intended application, i.e. different conductivities and permittivities, in different combinations.

For example, for the potential measurement of multiphase fluid from an oil field, various individual values, and combinations thereof, of the conductivity and permittivity of the phases likely to be encountered when using the apparatus and method of the invention are shown in Table 1 below.

TABLE 1

| Property/Fluid | Air | Oil | Water |
|---|---|---|---|
| Conductivity (S/m) | 0 | 0 | 0.5, 0.15, 0.25, 0.35, 0.45, 0.55, 1, 5 |
| Dielectric Constant ($\varepsilon/\varepsilon_0$) | 1 | 1, 2, 2.8, 3, 3.2, 4, 5, 6.03, 7.4, 10 | 80 |

Using this stored data and model that correlates simultaneous responses from the system to changes in permittivity and conductivity, the degree of correlation between the measurements and the electrical properties may be identified. The model may be validated using three-phase combinations of the fluids/solids of interest.

The apparatus 2 further comprises a comparator 42 for comparing a measured value of an amplitude of a measured complex voltage with the first stored data to provide a selected value of electrical permittivity correlated to the measured amplitude value, and/or for comparing a measured value of a phase angle of a measured complex voltage with the second stored data of a complex voltage to provide a selected value of electrical conductivity correlated to the measured phase angle value.

Figure 2:
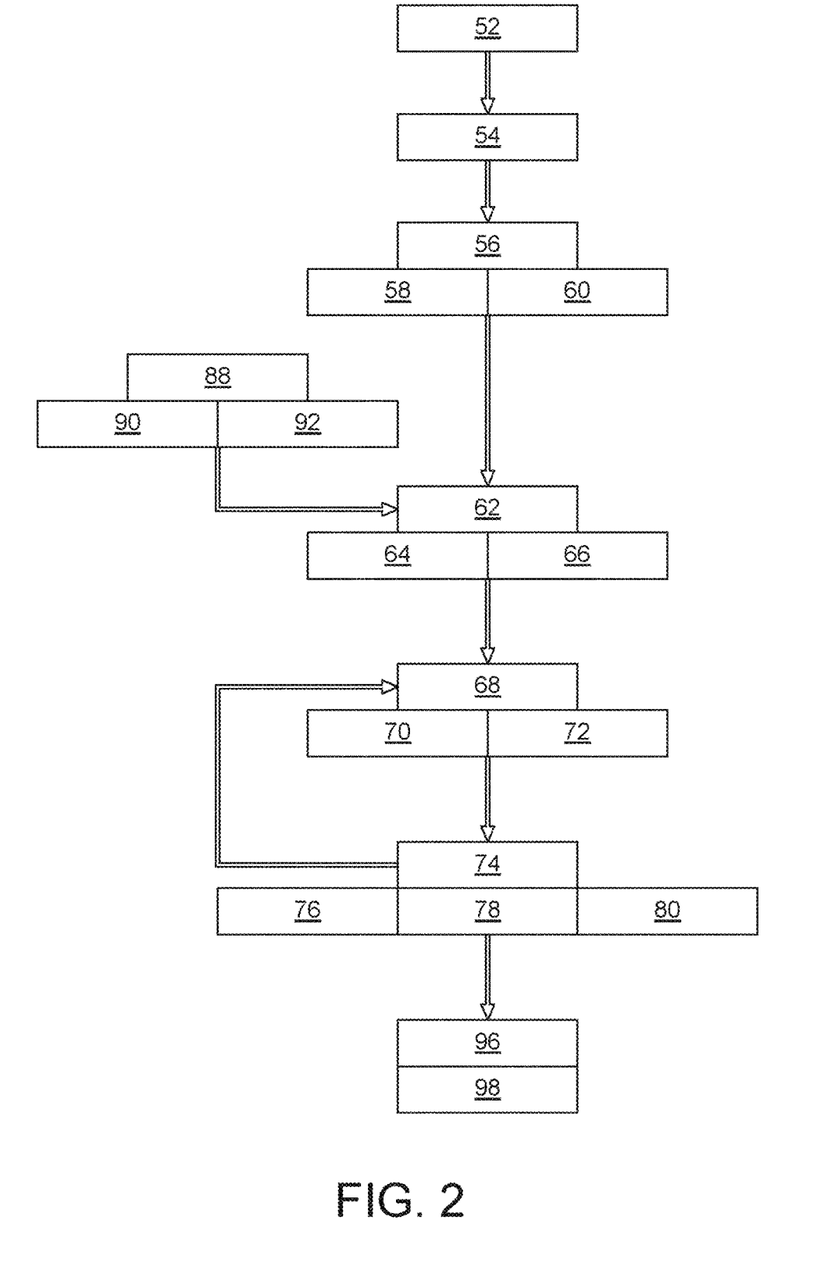
FIG. 2 is a schematic process flow of a method of monitoring a multiphase flow using the apparatus of FIG. 1.

Accordingly, in the preferred embodiment of the present invention, determination step 56, calculation step 62 and analysing step 68 function to:
1) Identify, from the amplitude and phase angle data of the induced complex voltage, the weight of both the displacement current induced by the electrically non-conductive phase, and the eddy current induced by the electrically conductive phase, in a multiphase fluid, typically a multiphase flow;
2) Derive, using the weight parameters and stored data correlating measured phase angle to electrical conductivity and measured amplitude to electrical permittivity, the associated permittivity and conductivity of the multiphase fluid;
3) Derive the volumetric fraction associated with electrically conductive and electrically non-conductive phases.

The apparatus 2 further comprises an imaging module 44 adapted to process the analysed data to produce image data in a form representing the multiphase fluid within the volume across at least a portion of a cross-sectional area of the volume. Preferably, the image data is provided to a display device 46 for visually displaying a sequence of images representing temporal changes in the multiphase fluid within the volume.

The method of monitoring, by magnetic induction tomography, a multiphase fluid within an interior volume defined by a body using the apparatus of FIG. 1 will now be described. The process flow is illustrated in FIG. 2.

The method comprises the step 52 of generating a magnetic field within the interior volume defined by the body. The magnetic field temporally varies according to at least one frequency, thereby to apply the varying magnetic field to a multiphase fluid within the volume, in FIG. 1 the volume being the flow conduit 6 of the pipe 4.

For example, an electromagnetic field is transmitted from one of the coils 10 into the multiphase flow 8. The multiphase flow 8, when the invention is being used in the oil industry, typically comprises an oil phase, and an aqueous phase, and optionally one or both of a solid phase and a gaseous phase.

The other coils 10 each receive an electromagnetic field from the eddy currents induced in the multiphase flow 8 and generates an output electrical signal therefrom. Each of the coils 10 can act as either a transmitting or receiving coil and can change between the two transmitting and receiving modes. As described above, an alternating electrical current, preferably having a frequency of from 1 kHz to 10 MHz, is switched through one of the coils 10 to generate from the respective energized coil 10 a local electromagnetic field which is transmitted into the fluid conduit 6.

Thus a varying electric current is passed through the transmitting coil 10, which may have the properties of a sine wave, or another form, e.g. square wave, and all other potential forms of varying current are encompassed by the present invention. The varying electric current passing through the transmitting coil 10 generates a varying electromagnetic flux through the multiphase flow 8 that is within the pipe 4. Depending on the physical properties of the different phases that the electromagnetic flux lines interrogate and in particular the electrical conductivity contrast between the phases, for example the oil and aqueous phases, a varying current is induced in any electrically conductive phase. This induced current in turn generates a secondary varying electromagnetic field that propagates through the pipe 4 and is picked up by each coil 10 that is used as a receiver. The secondary varying electromagnetic field therefore induces a varying current in the receiver coil 10, and this is associated with a corresponding induced complex voltage which has been produced by electromagnetic induction from at least one phase of the multiphase fluid within the volume. The induced complex voltage is measured by the voltage measuring system 22 in a measuring step 54.

The coils 10 can function in a fixed operating mode, i.e. one coil 10 acts as a transmitting coil and the other coil(s) 10 act(s) as one or more receiving coil(s), or in a dynamic operating mode, i.e. the coils 10 can be switched so as to alternate between functioning as a transmitting coil and as a receiving coil.

When more than two coils are provided, typically one coil may function as a transmitter and other coils may function as a receiver, so that, for example, at any point in time there is one coil that is transmitting and all of the other coils are receiving. Once all the receiver coil signals have been processed, one or more of the other coils becomes the transmitter and again the remainder are receivers and so forth.

It will be appreciated by those skilled in the art that the sequencing may take place in any order and that a complete cycle of measurements, that is, where every coil has been the transmitter once, can occur very rapidly with, e.g., 160 to 8000, or 500 to 5000, measurement cycles every second. This frequency is primarily limited only by the processing power of the processor 24. It will also be appreciated by those skilled in the art that after one complete cycle of measurements a mesh of properties is produced that can be processed to provide a mesh or image of the multiple phases across the section of the pipe.

Although this illustrated embodiment describes each coil being either a transmitter or receiver, alternatively, a configuration can be provided whereby certain coils are always transmitters and others are always receivers. In other embodiments coils can be enclosed within other coils so that dedicated transmitter and receiver coils are at the same location. Those skilled in the art will appreciate that many combinations are possible and all such combinations may be employed in this invention.

By comparing the driving and induced currents using appropriate processing in the processor 24, for example, the phase shift between the signals, allows the conductivity contrast between the materials of the multiphase flow to be computed.

The electromagnetic measurement as described above can provide phase measurements where there is an electrical conductivity contrast between the phases. This is possible when the different phases or constituents are static or flowing in a predominately electrically conducting (e.g. water) or electrically non-conducting (e.g. oil) primary phase.

In a step 56, the signal processor 24 determines, from the measured induced complex voltage, both an amplitude and a phase angle of the complex voltage. The phase angle of the complex voltage is determined by comparing the phase of the complex voltage and the phase of the magnetic field. This determination step 56 respectively provides amplitude data 58 and phase angle data 60.

In a subsequent step 62, first and second output data 64, 66 are calculated from the amplitude data 58 and phase angle data 60. In particular, the first output data 64 is calculated from the amplitude data 58 and the first output data 64 is a function of the electrical permittivity and electrical conductivity of the at least one phase of the multiphase fluid. The second output data 66 is calculated from the phase angle data 60, and the second output data 66 is a function of the electrical conductivity of the at least one phase of the multiphase fluid.

In a data storage step 88, first and second stored data 90, 92 are stored in the memory 40. The first stored data 90 represents a relationship between electrical permittivity of at least one known electrically non-conductive phase and amplitude of a complex voltage measured using a magnetic field of known properties. The second stored data 92 represents a relationship between electrical conductivity of at least one known electrically conductive phase and phase angle of a complex voltage measured using a magnetic field of known properties.

In step 62, a measured value of an amplitude of a measured complex voltage is compared with the first stored data 90 to provide a selected value of electrical permittivity correlated to the measured amplitude value. In addition, in step 62, a measured value of a phase angle of a measured complex voltage is compared with the second stored data 92 to provide a selected value of electrical conductivity correlated to the measured phase angle value.

In other words, the measured complex voltage can be interpreted to provide vales of electrical permittivity and electrical conductivity which represent the properties of the phases in the multiphase fluid.

In a subsequent step 68, the first and second output data 64, 66 are analysed in analyser 36 to generate analysed data 74 representing at least one property of at least one electrically non-conductive phase in the multiphase fluid and at least one property of at least one electrically conductive phase in the multiphase fluid.

In step 68, a first parameter 70 is calculated from the amplitude data 58. The first parameter 70 is related to a displacement current induced in at least one electrically non-conductive phase in the multiphase fluid and at least one electrically conductive phase in the multiphase fluid. The first parameter 70 is within the first output data 64. Correspondingly in step 68 a second parameter 72 is calculated from the phase angle data 60. The second parameter 72 is related to an eddy current induced in at least one electrically conductive phase in the multiphase fluid. The second parameter 72 is within the second output data 66.

In analysing step 68, the first and second output data 64, 66 are processed to generate first analysed data 76 representing the electrical permittivity of the at least one electrically non-conductive phase in the multiphase fluid and second analysed data 78 representing the electrical conductivity of the at least one electrically conductive phase in the multiphase fluid.

A third parameter 80 is calculated from the second parameter 72 related to the at least one electrically conductive phase. The third parameter 80 is related to a contribution to the displacement current of the first parameter by the at least one electrically conductive phase. The first analysed data 76 is generated by calculating, from the first parameter 70 and the third parameter 80, a contribution to the displacement current of the first parameter 70 by the at least one electrically non-conductive phase.

The analysed data 74 generated in step 68 represents, directly or indirectly, the respective phase fractions, preferably the volumetric phase fractions, of at least one electrically non-conductive phase in the multiphase fluid and at least one electrically conductive phase in the multiphase fluid.

The steps 56, 62 and 68 are performed by at least one processor.

The method further comprises the step 96 of processing the analysed data 74 to produce image data 98 in a form representing the multiphase fluid within the volume across at least a portion of a cross-sectional area of the volume. A sequence of images representing temporal changes in the multiphase fluid within the volume may be visually displayed.

In an alternative embodiment, each first coil 10 mat be circumferentially offset in a direction around the pipe 4, with respect to a respective adjacent second coil 12, to reduce or minimise direct electromagnetic coupling between the respective first and second coils 10, 12.

As described in the Applicant's prior patent specifications, the electrical current may be selectively switched through selected first coils 10 in an array to generate from each energized coil a local electromagnetic field. Typically, an impedance (not shown) connected to at least some of the respective selected coils in the array is provided to modify the magnitude of the local electromagnetic field generated from the respective energized coil element.

In one embodiment, the electrical current may be selectively switched through selected coils in the array to provide a composite electromagnetic field generated from the energized first coils 10, when transmitting, and the energized first coils 10 have a controllable focal point within the pipe 4.

In another embodiment, the electrical current may be selectively switched through selected first coils 10 in the array 10 to provide a composite electromagnetic field received by the second coils 12, when receiving, from a controllable focal point within the pipe 4. The controllable focal point may be scanned across the array of first and second coils 10, 12 to scan the generated electromagnetic field across a cross-section of the pipe 4 and/or along a flow direction along the pipe 4. The scanning of the controllable focal point may be across a plurality of points to provide a pixelated image of the multiphase flow.

As described in the Applicant's prior patent specifications as summarised above, in alternative embodiments respective pairs of transmitting and receiving coils may be separated by a known fixed distance along the flow direction of the pipe. Each pair of transmitting and receiving coils may be operated as described above and can provide independent meshes or images of the flow at two points along the pipe. It is possible to cross-correlate the measurements from two transmitter/receiver pairs, in order to establish the time-of-flight of features that represent different phases in the multiphase flow. The time difference between the features provides the time it takes for the phase to travel over the fixed distance. Those skilled in the art will appreciate that the velocity of this phase is readily computed from this information. Correspondingly, a velocity profile across the cross section of the pipe may be obtained. That is, a mesh or image of velocities can be produced that can be used to establish the velocity differences between the primary/continuous phase, and any other phase. Such velocities can be obtained when the primary or continuous phase is either conducting (e.g. water) or non-conducting fluid (e.g. oil).

Furthermore, alternative embodiments of the monitoring apparatus of the present invention for monitoring a multiphase flow in a pipe using magnetic induction tomography may comprise a plurality of, for example two, annular arrays of the transmitter/receiver coils 10, 12 disposed around the pipe 4 which defines therein an imaging space. In the first array, each first coil 10 is adapted to transmit an electromagnetic field when energized by an input electrical signal, and in the second array each second coil 12 is adapted to receive an electromagnetic field and generate an output electrical signal.

The present invention will now be described further with reference to the following non-limiting Example.

EXAMPLE

Figure 5:
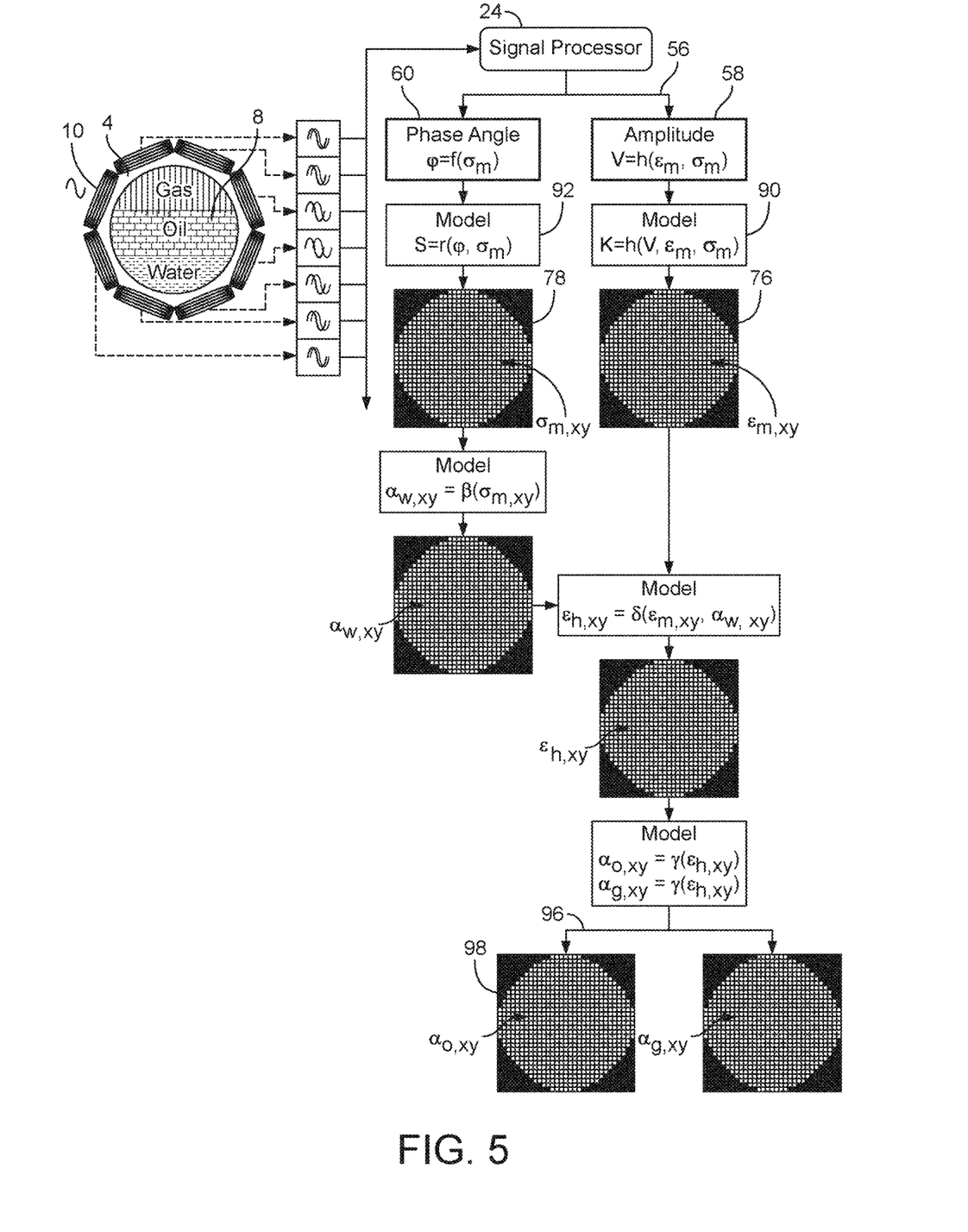
FIG. 5 is a schematic process flow used in an example of a method of monitoring a multiphase flow using the apparatus of FIG. 1.

A monitoring apparatus 2 as shown in FIG. 1 is provided, as also shown in FIG. 5. A multiphase flow 8 flows along the flow conduit 6 defined by the pipe 4. The driver 20 provides an alternating current to the coils 10 to generate a magnetic field within the multiphase flow 8, as shown by step 52 of FIG. 2.

The voltage measuring system 22 receives and in step 54 measures the induced complex voltages, representative of the electromagnetic properties of the mixed multiphase flow 8.

The signal processor 24 processes the measured complex voltages from a number of coils 10 in step 56 to output both phase angle data 60 and amplitude data 58.

Table 1 explains the symbols shown in FIG. 5.

TABLE 1

| Symbol | |
|---|---|
| $\phi$ | Phase angle |
| $\sigma$ | Conductivity |
| V | Voltage amplitude |
| $\varepsilon$ | Permittivity |

TABLE 1-continued

| Symbol | |
|---|---|
| $\alpha$ | Volumetric fraction |
| m | Mixture |
| w | Water |
| o | Oil |
| g | Gas |
| xy | Pixel position |
| h | hydrocarbon |

Figure 3:
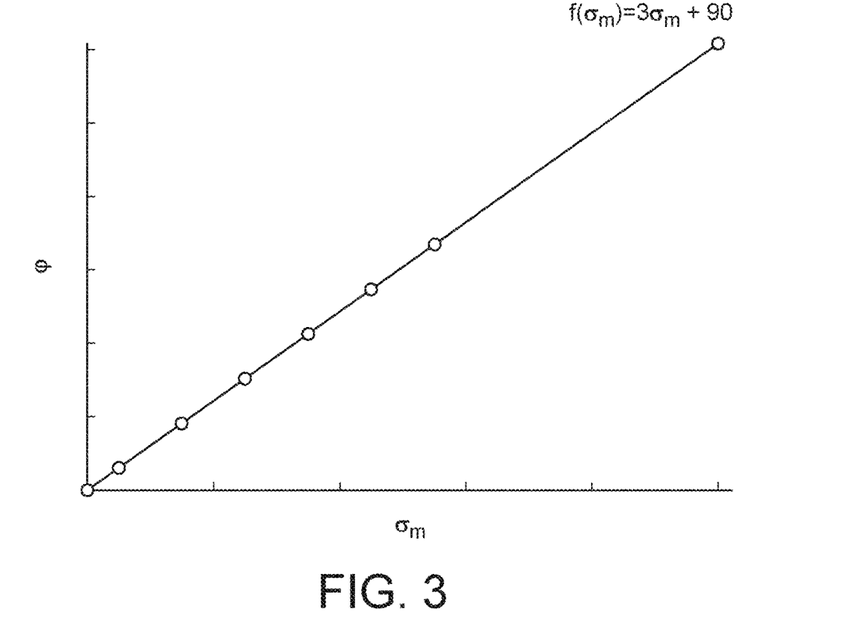
FIG. 3 is a graph showing the relationship between phase angle and conductivity according to a first model used in an example of a method of monitoring a multiphase flow using the apparatus of FIG. 1.

The phase angle, $\phi$, is a function of the mixed electrical conductivity, $\sigma_m$, in a multiphase flow: $\phi=f(\sigma_m)$, where $\sigma$ is conductivity and the suffix m means for the mixed multiphase flow. As show in FIG. 3, the relationship can be expressed by a linear model $f(\sigma_m)=3\sigma_m+90$. The model can be derived from either simulation or experimental data and can take another form other than linear. However, FIG. 3 shows a typical model to be used in an example of the present invention. The relationship is stored as the second stored data 92 stored in the memory 40 in data storage step 88.

Figure 4:
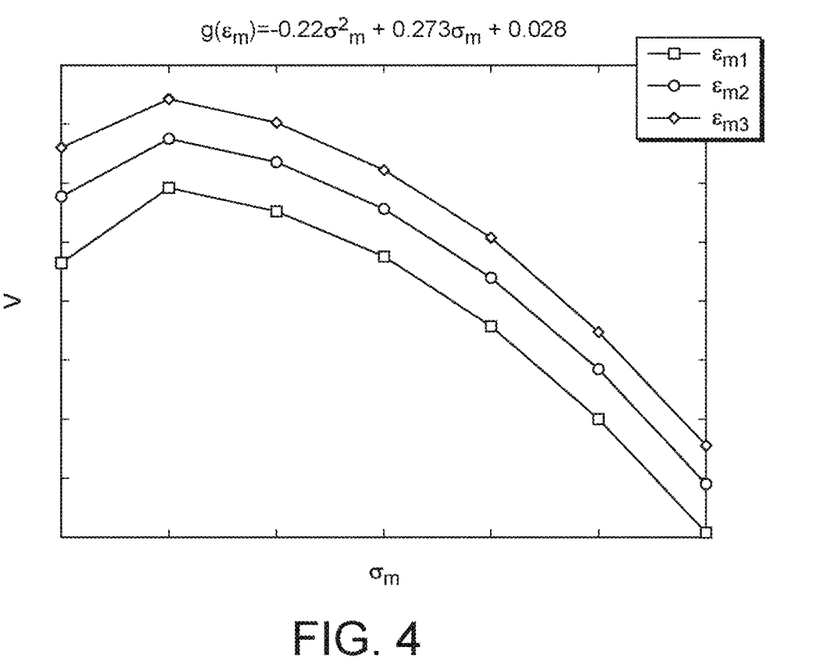
FIG. 4 is a graph showing the relationship between voltage and conductivity, at different permittivity values, according to a second model used in an example of a method of monitoring a multiphase flow using the apparatus of FIG. 1.

The voltage amplitude, V, is a function of both the mixed electrical conductivity, $\sigma_m$, and the mixed relative electrical permittivity, $\varepsilon_m$, of a multiphase flow: $V=h(\varepsilon_m, \sigma_m)$. As show in FIG. 4, the relationship between the mixed conductivity and mixed relative permittivity can be expressed by a quadratic model, for example: $g(\varepsilon_m)=-0.22\sigma_m^2+0.0273\sigma_m+0.028$ for a given $\varepsilon_{m_i}$ for i={1, 2, ..., n}. The model $g(\varepsilon_m)$ can be derived from either simulation or experimental data and can take another form other than quadratic. However, FIG. 4 shows a typical model to be used in an example of the present invention. The relationship is stored as the first stored data 90 stored in the memory 40 in data storage step 88.

Then, using comparison step 62 as described above, the first stored data 90 provides first output data 64 which is a function of the electrical permittivity and electrical conductivity of the multiphase flow and the second stored data 92 provides second output data 66 which is a function of the electrical conductivity of the multiphase flow.

Thereafter, the first and second output data 64, 66 are analysed in analyser 36 to generate the first analysed data 76 to generate the respective first analysed data representing electrical permittivity of the electrically non-conductive phase in the multiphase fluid and second analysed data 78 representing the electrical conductivity of the at least one electrically conductive phase in the multiphase fluid.

A pre-calculated or real time iterated sensitivity map S is applied to the second analysed data 78, by which the mixed conductivity distribution can be reconstructed, using the measured phase angle data, in each pixel in a pre-defined grid structure encompassing the cross-section of the pipe 4. From the reconstructed mixed conductivity distribution, using the analysing step 68 the analysed data 74 can be used to derive the volumetric fraction of water in each pixel using another model, for example the model $\alpha_{w,xy}=\beta(\sigma_{m,xy})$.

A pre-calculated or real time iterated sensitivity map K is applied to the first analysed data 76, by which the mixed permittivity distribution can be reconstructed, using the measured amplitude data, in each pixel in a pre-defined grid structure encompassing the cross-section of the pipe 4.

Also in the analysing step 68 the analysed data 74 can be used by combining the reconstructed mixed relative permittivity with the derived water volumetric fraction, so that the mixed relative permittivity for the hydrocarbon phase can be derived in each pixel using another model, for example the model $\varepsilon_{h,xy}=\delta(\varepsilon_{m,xy}, \alpha_{w,xy})$.

Thereafter, using step 96, knowing the hydrocarbon phase distribution, the respective phases such as the oil and gas volumetric fraction can be derived using a further model, for example the model $\alpha_{o,xy}=\gamma(\varepsilon_{g,xy})$, $\alpha_{g,xy}=\gamma(\varepsilon_{h,xy})$. This data can be visually displayed as image data 98.

Various other embodiments of the monitoring apparatus and method of the present invention within the scope of the appended claims will readily be apparent to those skilled in the art.

The invention claimed is:

1. A magnetic induction tomographic apparatus for monitoring a multiphase fluid within an interior volume defined by a body, the apparatus comprising:
   a a magnetic field generator adapted to generate a magnetic field within the interior volume defined by the body, the magnetic field temporally varying according to at least one frequency, thereby to apply the varying magnetic field to a multiphase fluid within the volume;
   b a voltage detector adapted to measure an induced complex voltage which has been produced by electromagnetic induction from at least one phase of the multiphase fluid within the volume;
   c a signal processor for determining, from the measured induced complex voltage, both an amplitude and a phase angle of the complex voltage, thereby respectively to provide amplitude data and phase angle data;
   d a data processor for calculating, from the amplitude data and phase angle data, first output data from the amplitude data and second output data from the phase angle data, wherein the first output data is a function of the electrical permittivity and electrical conductivity of the at least one phase of the multiphase fluid and the second output data is a function of the electrical conductivity of the at least one phase of the multiphase fluid;
   e an analyser for processing the first and second output data to generate analysed data representing at least one property of at least one electrically non-conductive phase in the multiphase fluid and at least one property of at least one electrically conductive phase in the multiphase fluid; and
   f an imaging module adapted to process the analysed data to produce image data in a form representing the multiphase fluid within the volume across at least a portion of a cross-sectional area of the volume.

2. An apparatus according to claim 1 wherein the signal processor is adapted to determine the phase angle of the complex voltage by comparing the phase of the complex voltage and the phase of the magnetic field generated by the magnetic field generator.

3. An apparatus according to claim 1, wherein the analyser is adapted to generate analysed data which represents, directly or indirectly, the respective phase fractions of at least one electrically non-conductive phase in the multiphase fluid and at least one electrically conductive phase in the multiphase fluid.

4. An apparatus according to claim 3 wherein the analysed data represents, directly or indirectly, the respective volumetric phase fractions of at least one electrically non-conductive phase in the multiphase fluid and at least one electrically conductive phase in the multiphase fluid.

5. An apparatus according to claim 1, wherein the data processor comprises a first module adapted to calculate from the amplitude data a first parameter related to a displacement current induced in at least one electrically non-conductive phase in the multiphase fluid and at least one electrically conductive phase in the multiphase fluid, the first parameter being within the first output data, and a second module adapted to calculate from the phase angle data a second parameter related to an eddy current induced in at least one electrically conductive phase in the multiphase fluid, the second parameter being within the second output data.

6. An apparatus according to claim 5 wherein the analyser is adapted to process the first and second output data to generate first analysed data representing the electrical permittivity of the at least one electrically non-conductive phase in the multiphase fluid and second analysed data representing the electrical conductivity of the at least one electrically conductive phase in the multiphase fluid.

7. An apparatus according to claim 1 further comprising a memory in communication with the signal processor, the data processor, the analyser, or a combination thereof, wherein the memory comprises first stored data representing a relationship between the electrical permittivity of the at least one known electrically non-conductive phase and amplitude of the complex voltage measured using the magnetic field of known properties and second stored data representing a relationship between the electrical conductivity of the at least one known electrically conductive phase and phase angle of the complex voltage measured using the magnetic field of known properties.

8. An apparatus according to claim 7 further comprising a comparator for comparing a measured value of an amplitude of a measured complex voltage with the first stored data to provide a selected value of electrical permittivity correlated to the measured amplitude value, and/or for comparing a measured value of a phase angle of a measured complex voltage with the second stored data to provide a selected value of electrical conductivity correlated to the measured phase angle value.

9. An apparatus according to claim 1 further comprising a display device for visually displaying a sequence of images representing temporal changes in the multiphase fluid within the volume.

10. An apparatus according to claim 1 which is adapted to monitor a multiphase fluid flow in a body formed as a pipe.

11. A magnetic induction tomographic apparatus for monitoring a multiphase fluid within an interior volume defined by a body, the apparatus comprising:
   a a magnetic field generator adapted to generate a magnetic field within the interior volume defined by the body, the magnetic field temporally varying according to at least one frequency, thereby to apply the varying magnetic field to a multiphase fluid within the volume;
   b a voltage detector adapted to measure an induced complex voltage which has been produced by electromagnetic induction from at least one phase of the multiphase fluid within the volume;
   c a signal processor for determining, from the measured induced complex voltage, both an amplitude and a phase angle of the complex voltage, thereby respectively to provide amplitude data and phase angle data;
   d a data processor for calculating, from the amplitude data and phase angle data, first output data from the amplitude data and second output data from the phase angle data, wherein the first output data is a function of the electrical permittivity and electrical conductivity of the at least one phase of the multiphase fluid and the second output data is a function of the electrical conductivity of the at least one phase of the multiphase fluid, wherein the data processor comprises:

a first module adapted to calculate from the amplitude data a first parameter related to a displacement current induced in at least one electrically non-conductive phase in the multiphase fluid and at least one electrically conductive phase in the multiphase fluid;

a second module adapted to calculate from the phase angle data a second parameter related to an eddy current induced in at least one electrically conductive phase in the multiphase fluid; and a third module adapted to calculate, from the second parameter related to the at least one electrically conductive phase, a third parameter, the third parameter being related to a contribution to the displacement current of the first parameter by the at least one electrically conductive phase; and e an analyser for processing the first and second output data to generate analysed data representing at least one property of at least one electrically non-conductive phase in the multiphase fluid and at least one property of at least one electrically conductive phase in the multiphase fluid.

12. An apparatus according to claim 11 wherein the third module is adapted to calculate from the first parameter and the third parameter a contribution to the displacement current of the first parameter by the at least one electrically non-conductive phase thereby to generate the first analysed data.

13. A method of monitoring, by magnetic induction tomography, a multiphase fluid within an interior volume defined by a body, the method comprising the steps of:

a generating a magnetic field within the interior volume defined by the body, the magnetic field temporally varying according to at least one frequency, thereby to apply the varying magnetic field to a multiphase fluid within the volume;

b measuring, using a voltage detector, an induced complex voltage which has been produced by electromagnetic induction from at least one phase of the multiphase fluid within the volume;

c determining, from the measured induced complex voltage, both an amplitude and a phase angle of the complex voltage, thereby respectively to provide amplitude data and phase angle data;

d calculating, from the amplitude data and phase angle data, first output data from the amplitude data and second output data from the phase angle data, wherein the first output data is a function of the electrical permittivity and electrical conductivity of the at least one phase of the multiphase fluid and the second output data is a function of the electrical conductivity of the at least one phase of the multiphase fluid;

e analysing the first and second output data to generate analysed data representing at least one property of at least one electrically non-conductive phase in the multiphase fluid and at least one property of at least one electrically conductive phase in the multiphase fluid, wherein steps c, d and e are performed by at least one processor; and f processing the analysed data to produce image data in a form representing the multiphase fluid within the volume across at least a portion of a cross-sectional area of the volume, and optionally further comprising the step of visually displaying a sequence of images representing temporal changes in the multiphase fluid within the volume.

14. A method according to claim 13 wherein in step c the phase angle of the complex voltage is determined by comparing the phase of the complex voltage and the phase of the magnetic field.

15. A method according to claim 13, wherein in step e, the analysed data represents, directly or indirectly, the respective phase fractions of at least one electrically non-conductive phase in the multiphase fluid and at least one electrically conductive phase in the multiphase fluid.

16. A method according to claim 15 wherein in step e, the analysed data represents, directly or indirectly, the respective volumetric phase fractions of at least one electrically non-conductive phase in the multiphase fluid and at least one electrically conductive phase in the multiphase fluid.

17. A method according to claim 13, wherein in step d, a first parameter related to a displacement current induced in at least one electrically non-conductive phase in the multiphase fluid and at least one electrically conductive phase in the multiphase fluid, the first parameter being within the first output data, is calculated from the amplitude data and a second parameter related to an eddy current induced in at least one electrically conductive phase in the multiphase fluid, the second parameter being within the second output data, is calculated from the phase angle data.

18. A method according to claim 17 wherein in step e, the first and second output data are processed to generate first analysed data representing the electrical permittivity of the at least one electrically non-conductive phase in the multiphase fluid and second analysed data representing the electrical conductivity of the at least one electrically conductive phase in the multiphase fluid.

19. A method according to claim 13 further comprising the step of storing in a memory first stored data representing a relationship between electrical permittivity of at least one known electrically non-conductive phase and amplitude of a complex voltage measured using a magnetic field of known properties and second stored data representing a relationship between electrical conductivity of at least one known electrically conductive phase and phase angle of a complex voltage measured using a magnetic field of known properties.

20. A method according to claim 13 which monitors a multiphase fluid flow in a body formed as a pipe.

21. A method of monitoring, by magnetic induction tomography, a multiphase fluid within an interior volume defined by a body, the method comprising the steps of:

a generating a magnetic field within the interior volume defined by the body, the magnetic field temporally varying according to at least one frequency, thereby to apply the varying magnetic field to a multiphase fluid within the volume;

b measuring, using a voltage detector, an induced complex voltage which has been produced by electromagnetic induction from at least one phase of the multiphase fluid within the volume;

c determining, from the measured induced complex voltage, both an amplitude and a phase angle of the complex voltage, thereby respectively to provide amplitude data and phase angle data;

d calculating, from the amplitude data and phase angle data, first output data from the amplitude data and second output data from the phase angle data, wherein the first output data is a function of the electrical permittivity and electrical conductivity of the at least one phase of the multiphase fluid and the second output data is a function of the electrical conductivity of the at least one phase of the multiphase fluid, wherein a first parameter related to a displacement current induced in at least one electrically non-conductive phase in the multiphase fluid and at least one electrically conductive phase in the multiphase fluid is calculated from the amplitude data, and a second parameter related to an eddy current induced in at least one electrically conductive phase in the multiphase fluid is calculated from the phase angle data; and e analysing the first and second output data to generate analysed data representing at least one property of at least one electrically non-conductive phase in the multiphase fluid and at least one property of at least one electrically conductive phase in the multiphase fluid, wherein steps c, d and e are performed by at least one processor, wherein a third parameter is calculated from the second parameter related to the at least one electrically conductive phase, the third parameter being related to a contribution to the displacement current of the first parameter by the at least one electrically conductive phase.

22. A method according to claim 21 wherein in step e the first analysed data is generated by calculating, from the first parameter and the third parameter, a contribution to the displacement current of the first parameter by the at least one electrically non-conductive phase.

23. A method of monitoring, by magnetic induction tomography, a multiphase fluid within an interior volume defined by a body, the method comprising the steps of:

a generating a magnetic field within the interior volume defined by the body, the magnetic field temporally varying according to at least one frequency, thereby to apply the varying magnetic field to a multiphase fluid within the volume;

b measuring, using a voltage detector, an induced complex voltage which has been produced by electromagnetic induction from at least one phase of the multiphase fluid within the volume;

c determining, from the measured induced complex voltage, both an amplitude and a phase angle of the complex voltage, thereby respectively to provide amplitude data and phase angle data;

d calculating, from the amplitude data and phase angle data, first output data from the amplitude data and second output data from the phase angle data, wherein the first output data is a function of the electrical permittivity and electrical conductivity of the at least one phase of the multiphase fluid and the second output data is a function of the electrical conductivity of the at least one phase of the multiphase fluid;

e analysing the first and second output data to generate analysed data representing at least one property of at least one electrically non-conductive phase in the multiphase fluid and at least one property of at least one electrically conductive phase in the multiphase fluid, wherein steps c, d and e are performed by at least one processor;

f storing in a memory first stored data representing a relationship between electrical permittivity of at least one known electrically non-conductive phase and amplitude of a complex voltage measured using a magnetic field of known properties and second stored data representing a relationship between electrical conductivity of at least one known electrically conductive phase and phase angle of a complex voltage measured using a magnetic field of known properties; and g comparing a measured value of an amplitude of a measured complex voltage with the first stored data to provide a selected value of electrical permittivity correlated to the measured amplitude value, and/or comparing a measured value of a phase angle of a measured complex voltage with the second stored data to provide a selected value of electrical conductivity correlated to the measured phase angle value.

* * * * *